United States Patent [19]

Mustain

[11] Patent Number: 4,829,547
[45] Date of Patent: May 9, 1989

[54] METHOD AND APPARATUS FOR TAKING TOMOGRAPHIC X-RAYS

[75] Inventor: Lewis B. Mustain, Cincinnati, Ohio

[73] Assignee: Liebel-Flarsheim, Cincinnati, Ohio

[21] Appl. No.: 44,643

[22] Filed: May 1, 1987

[51] Int. Cl.⁴ .................................................. G01N 23/00
[52] U.S. Cl. ........................................ 378/21; 378/196; 378/197
[58] Field of Search .............................. 378/21, 23–27, 378/39, 193, 195–197, 209

[56] References Cited

U.S. PATENT DOCUMENTS

| | | | |
|---|---|---|---|
| 2,235,143 | 3/1941 | Colcher | 378/26 |
| 3,708,664 | 1/1973 | Bock et al. | 378/22 |
| 3,743,843 | 7/1973 | Reser et al. | 378/27 |
| 3,809,886 | 5/1974 | Cochran et al. | 378/23 |
| 3,838,286 | 9/1974 | Prendergast et al. | 378/26 |
| 4,082,955 | 4/1978 | Sell | 378/26 |
| 4,087,694 | 5/1978 | Hellstrom et al. | 378/195 |
| 4,093,863 | 6/1978 | Zacher, Jr. | 378/4 |
| 4,095,110 | 6/1978 | Bunch | 378/26 |
| 4,139,776 | 2/1979 | Hellstrom | 378/25 |
| 4,145,613 | 3/1979 | Bunch | 378/26 |
| 4,211,927 | 7/1980 | Hellstrom et al. | 378/26 |
| 4,213,050 | 7/1980 | Meek | 378/26 |
| 4,315,156 | 2/1982 | Sell | 378/26 |
| 4,365,344 | 12/1982 | Dornheim | 378/189 |
| 4,455,668 | 6/1984 | Warden | 378/21 |
| 4,733,487 | 5/1973 | Louche et al. | 378/26 |

FOREIGN PATENT DOCUMENTS 1495520 9/1967 France .
2133246 7/1984 United Kingdom .

Primary Examiner—Janice A. Howell
Assistant Examiner—John C. Freeman
Attorney, Agent, or Firm—Wood, Herron & Evans

[57] ABSTRACT

A method and apparatus capable of taking tomographic x-rays which can be easily adjusted to provide the desired cutting plane without moving the patient or x-ray mechanism in a vertical direction. The apparatus is provided an x-ray source and detection plate. The x-ray source and detection plate are each moveable about a predetermined path independently of each other so as to provide any desired cutting plane.

5 Claims, 7 Drawing Sheets

METHOD AND APPARATUS FOR TAKING TOMOGRAPHIC X-RAYS

BACKGROUND OF THE INVENTION

The present invention is directed to a method and apparatus for taking x-rays which is particularly adaptable for use in the tomographic mode.

Tomography is a well known method of taking x-ray pictures to obtain an x-ray picture of a single plane through a patient wherein a selected layer of a patient or object is clearly imaged and the overlaying and underlaying portion is seen in blurred form. The basic mechanism used to obtain such an x-ray picture is the creation of relative motion between the x-ray beam, the patient and the x-ray detector screen in such a way that the x-ray beam sweeps through the patient in all areas except one "pivotal" plane in which the beam does not move relative to the patient. The image at this plane is clearly transferred to the x-ray detector while all other areas of the patient above and below the plane are blurred and indistinct on the detector due to the relative motion. The particular plane that is imaged is adjusted by either moving the patient in a vertical manner or by vertically moving the mechanism used to move the x-ray source and detector. The movement of the x-ray source, the patient and the detector are typically mechanically linked in some manner usually requiring a series of hydraulics, springs and weights, and various mechanical, or electrical-mechanical means to synchronize the required motion. Such mechanisms must be maintained with care so as to assure accurate movement in order to obtain clear tomograhic pictures.

Applicant's invention provides an improved method and apparatus which overcomes or minimizes the problems of the prior art.

SUMMARY OF THE INVENTION

In one aspect of the present invention there is provided an improved apparatus for taking tomographic x-rays. The apparatus has a patient support surface, an x-ray source, an aiming head for directing the x-ray source toward the patient on the support surface and an x-ray detection plate for receiving the x-rays emitted. Means are provided for moving the x-ray source along a first predetermined path. The aiming head is provided with means for aiming each ray from the x-ray source at a fixed point within the patient as it moves along the predetermined path. Means are also provided for moving the detection plate along a second predetermined path. Control means are provided for controlling rate and amount of movement of the x-ray source along the first predetermined path, aiming of the head and moving the detection plate along the second predetermined path so as to provide a clear x-ray image along a single preselected cutting plane on the patient.

In another aspect of the present invention there is provided a method of taking tomographic x-rays which comprises the steps of: providing a patient support surface for receiving a patient thereon, providing an x-ray emitting head having a source of x-ray which may be considered as a beam consisting of many diverging rays, providing an x-ray detection plate for detecting the x-rays emitted from the head, moving the head along a first predetermined path, aiming the x-rays emitted from the head at a predetermined point as the head is moved along first predetermined path, moving the detection plate along a second predetermined path and controlling the rate and amount of movement of the means for moving the head, means for aiming the x-ray source and means for moving said detection plate so as to provide a clear x-ray picture along a preselected cutting plane.

DETAILED DESCRIPTION OF THE DRAWINGS

Figure 1:
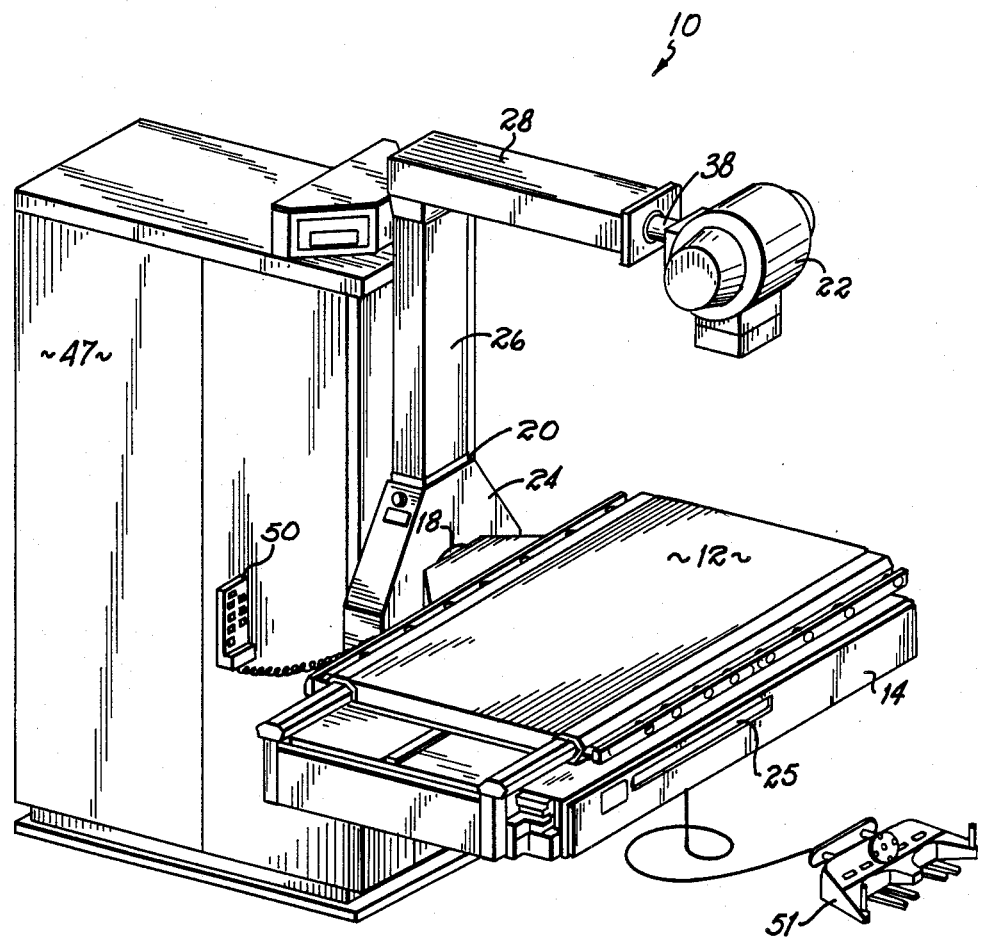
FIG. 1 is a perspective view of an apparatus made in accordance with the present invention.
Figure 4:
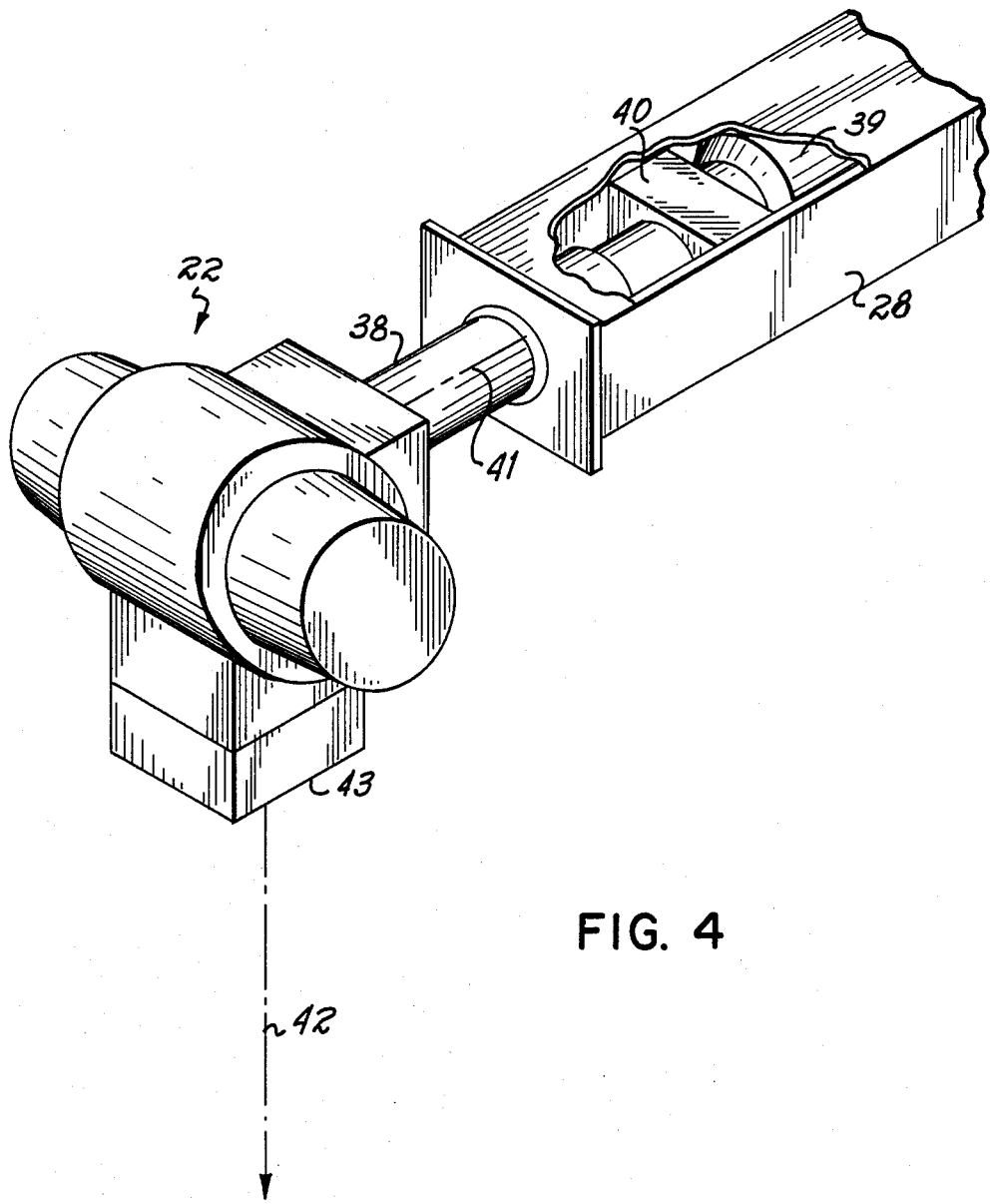
Figure 5:
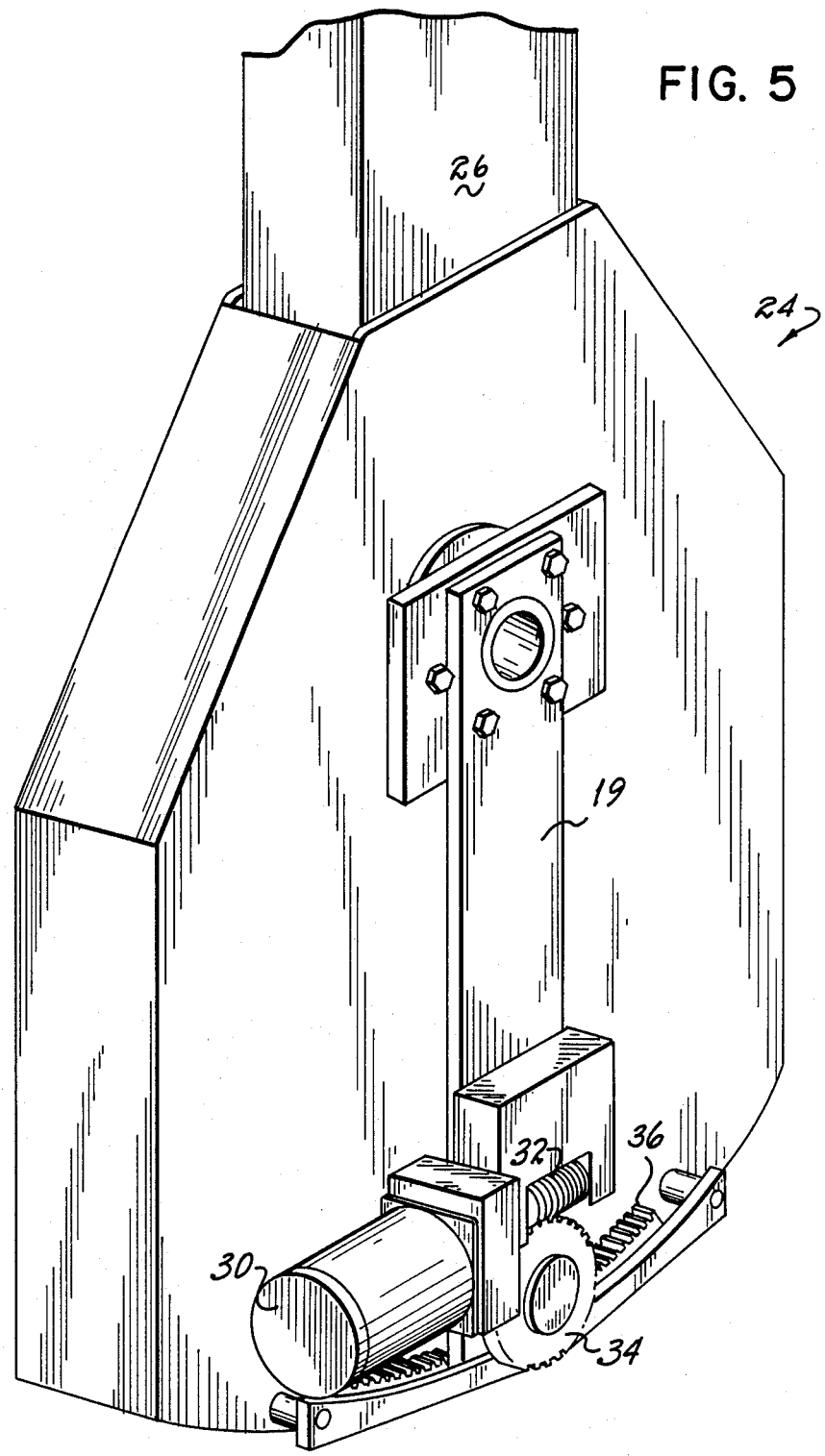

FIG. 3 A, B, C are diagrammatical representations of the method of operation of the apparatus of FIG. 1;

FIG. 4 is a perspective view of a portion of the apparatus of FIG. 1 illustrating the x-ray head assembly and the mechanism used to aim the x-ray head assembly; and FIG. 5 is an enlarged fragmentary view of the mechanism used to drive the x-ray source.

DETAILED DESCRIPTION OF THE INVENTION

Figure 2:
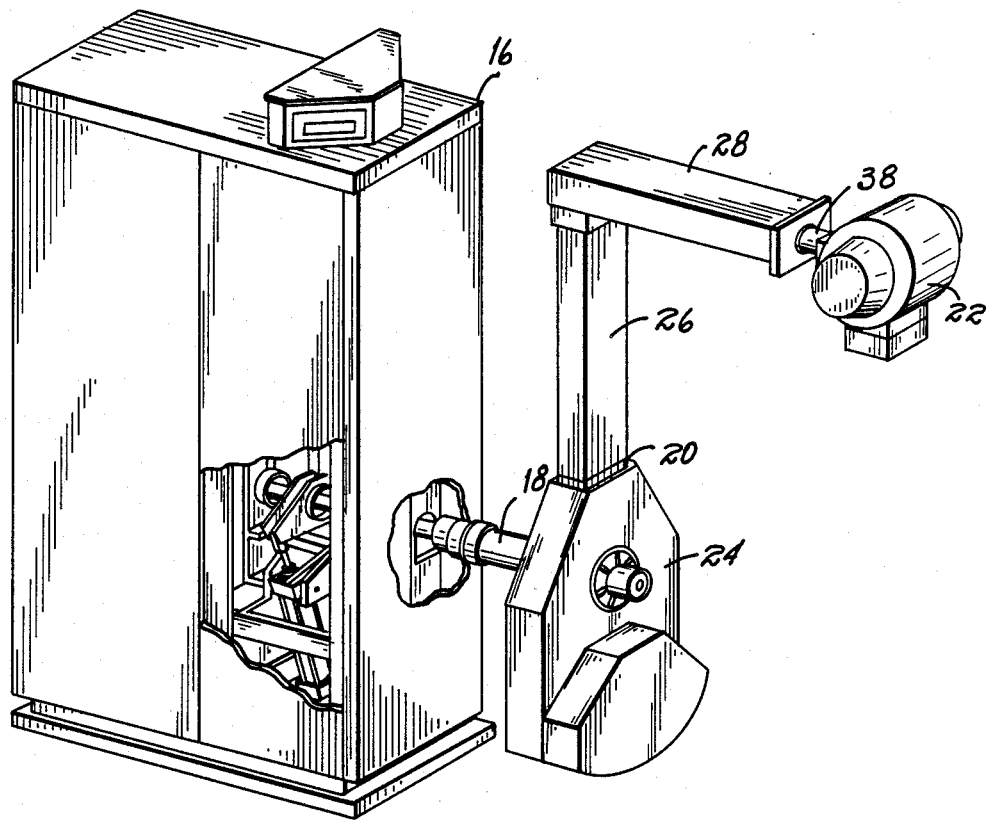
FIG. 2 is an exploded view of the apparatus of FIG. 1 with the patient support surface and filmer housing removed.

Referring to FIGS. 1 and 2 there is illustrated an x-ray apparatus 10 made in accordance with the present invention. The apparatus 10 comprises a patient support surface 12 which is slidably mounted on a filmer cassette housing 14. The filmer cassette housing is pivotably mounted to the main body frame 16 by rotatable shaft 18. Also attached to rotatable shaft 18 is tomo arm 20 for moving the x-ray source 22 during operation of the apparatus 10 in the tomographic mode. The particular manner by which the tomo arm 20 and film cassette housing 14 are rotated may be done in any conventional manner, for example by the use of an electric motor or a hydraulic system. The tomo arm 20 comprises a base portion 24, a vertical extension 26 and a horizontal extension 28.

Referring to FIG. 5, the base portion 24 is provided with a mechanism to move tomo arm 20 along a predetermined path. The path upon which the tomo arm moves is, of course, dependent upon physical construction thereof. As illustrated the tomo arm is mounted so as to rotate about axle 18. Therefore, the movement of the tomo arm will be an arcuate path as will be more fully described herein. In the particular embodiment illustrated the tomo arm 20 is driven by motor 30 which upon appropriate command is activated to drive worm 32 which in turn drives worm gear 34 which is engaged by means of a shaft and a spur gear (not shown) to toothed member 36 affixed to base portion 24. The motor is affixed to the axle 18 by brace 19. Therefore when the motor is activated it causes toothed member 36 to be moved along its path and since toothed member 36 is affixed to the base portion 24, the tomo arm rotates about the axle 18.

The filmer housing has an opening 25 receiving an x-ray film cassette therein. The opening, if desired, may be provided with a gate assembly (not shown) for allowing or preventing entry therein. A gate assembly such as disclosed in co-pending application, Ser. No. 07/044,725, filed simultaneously herewith could be employed, and such application is hereby incorporated herein. A film driver 54 takes the film cassette and locates it appropriately in the x-ray window.

Referring to FIG. 4 there is illustrated an x-ray head 22 which houses an x-ray source. The head 22 is connected to horizontal extension 28 by support shaft 38 which is capable of being rotated about its axis 41 by motor 39. The motor 39 is mounted to extension 28 in any conventional manner. The motor 39 drives reduction unit 40 attached to shaft 38 thereby permitting rotation of shaft 38 which in turn rotates head 22 in either rotational direction as required. The head 22 is provided with an appropriate x-ray source therein as is well known in the art. The head 22 is also provided with an aperture (not shown) on end 43 which will be opened or closed upon receiving the appropriate command to allow x-rays to be emitted in the general direction illustrated by lines 42 to an x-ray window in filmer housing 14.

Figure 3A:
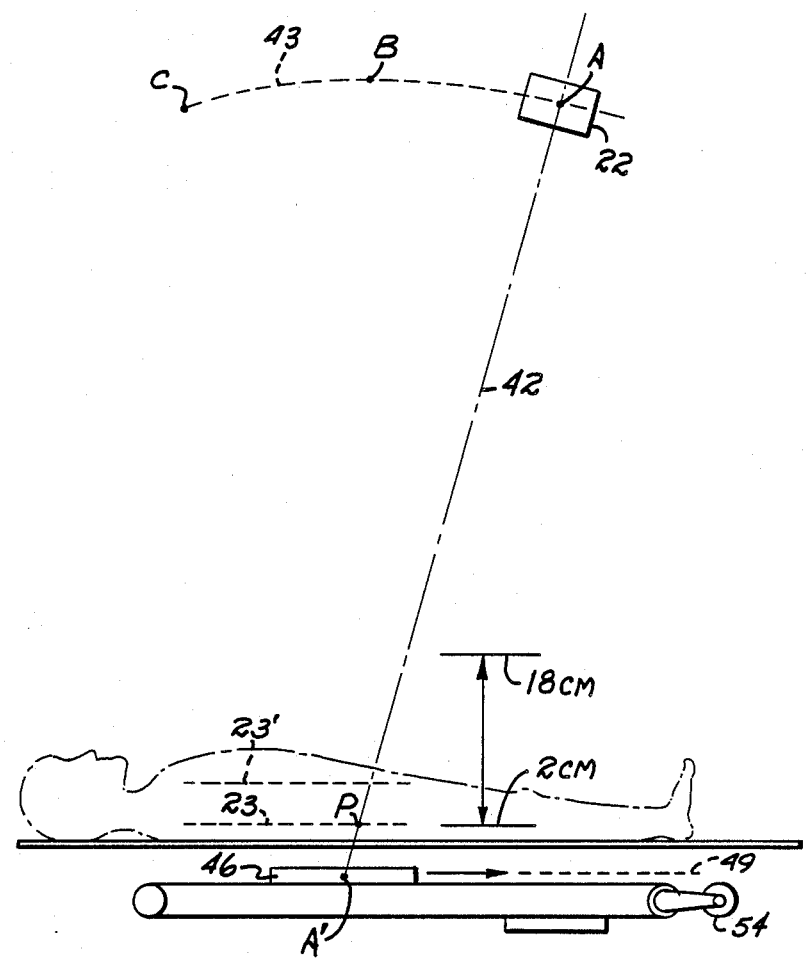
Figure 3B:
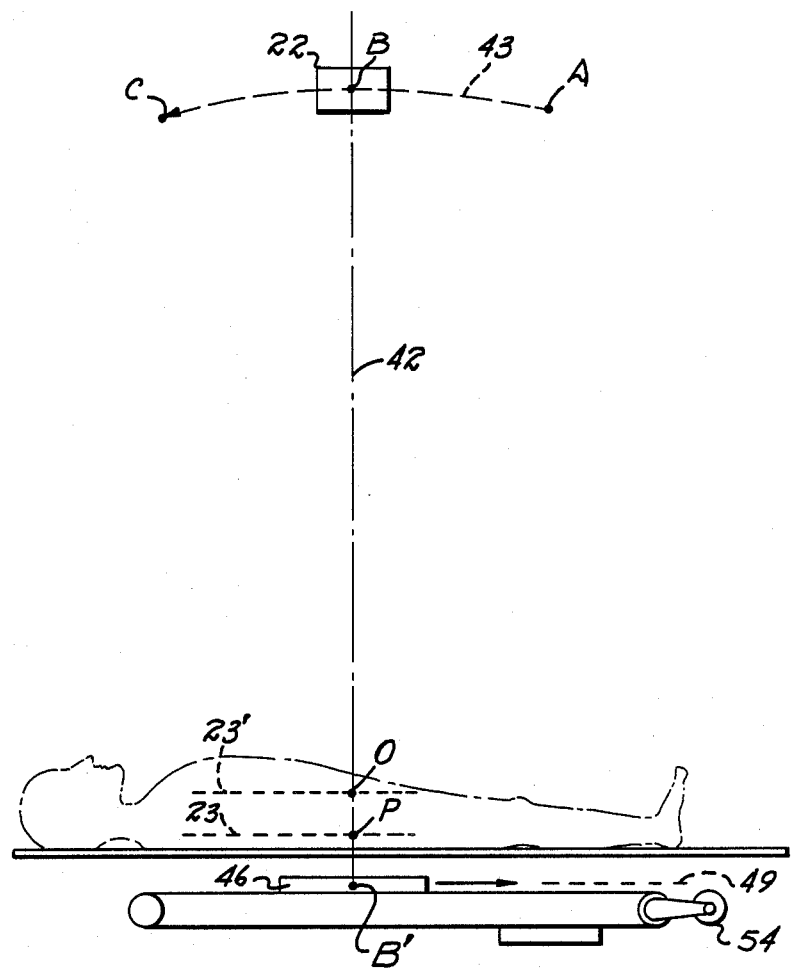

Referring to FIGS. 3A, B and C there is illustrated in diagrammatical form the operation of apparatus 10 in the tomographic mode. The theory of taking tomographic x-rays is well known to those skilled in the art which is well described in Radiological Imaging/The Theory Of Image Formation, Detection Processing-/volume 2 by Harrison H. Barrett and William Swindel published by Academic Press, Inc., N.Y., 1981, which is hereby incorporated by reference.

In tomographic devices of the prior art the fulcrum point is a predetermined point defined by the physical characteristics of the apparatus and the mechanical linkage between the film driver and movement of the x-ray source. In order to obtain different cutting planes the patient must be either moved vertically through the fulcrum point or the x-ray source and film drive apparatus must be moved vertically. Both options require various mechanical/electrical devices, hydraulics, springs and weights. In the present invention neither the patient, nor x-ray source or filmer is moved. Instead means are provided to select the fulcrum point as desired by varying the mathematical relations of the motions. This is accomplished by moving the x-ray source so that as it moves along its predetermined path the x-ray source continuously points at a preselected point. FIG. 3A illustrates the initial starting position A of the head 22. The tomo arm 20 is rotated about axle 18 through center position B illustrated in 3B and stops rotating when it reaches terminal position C illustrated in FIG. 3C. When the head 22 is in the initial position A, illustrated in FIG. 3A, the source of x-rays is aimed at a predetermined point P which defines a cutting plane 23 illustrated by dashed lines. Point P is the fulcrum point for the tomographic x-ray for the selected cutting plane 23. The cutting plane selected is limited only by the amount of movement required by the tomo arm 20, head 22 and detection plate 46. Cutting planes from about 2 cm to 18 cm can be accomplished without any difficulty. However, even greater selections can be easily accommodated.

Figure 3C:
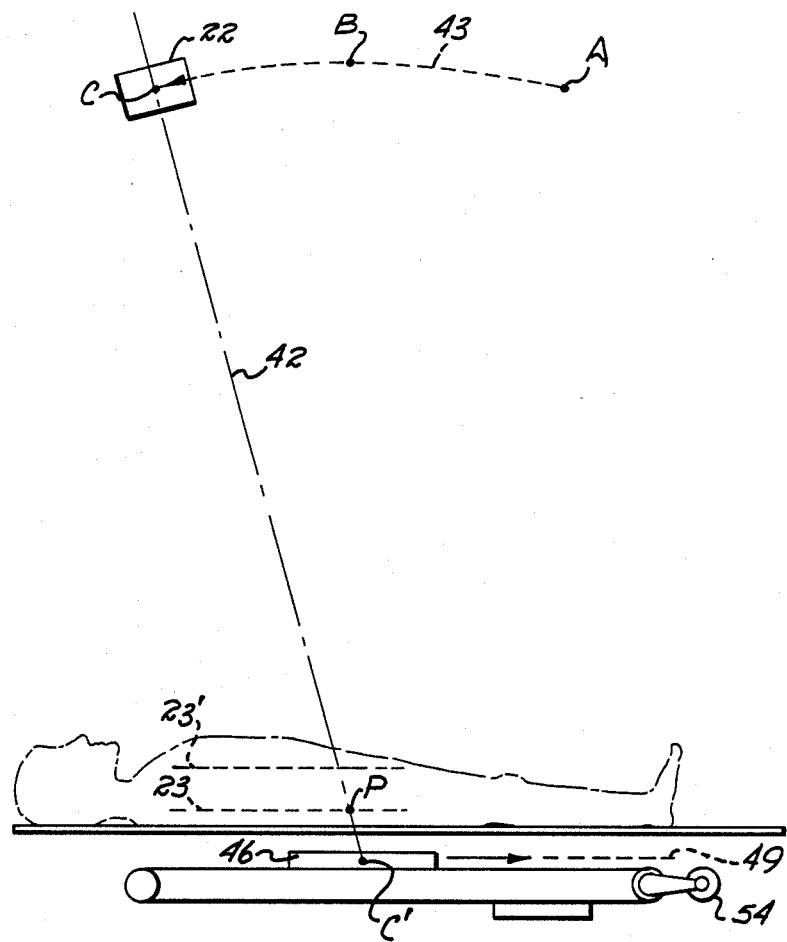

As the head is moved from position A in FIG. 3A to position C illustrated in FIG. 3C, the head 22 is continuously rotated according to a mathematical relationship so that it is continuously aimed at point P as it travels from position A to position C. In the particular embodiment illustrated this is accomplished by motor 39 which rotates head 22 as tomo arm is rotated from position A to position C. Therefore, everything that is not in the cutting plane 23 will become blurred. In order to adjust for a different cutting plane the aiming head position and motion are merely modified so that it aims at a different fulcrum point as it is moved from position A to position C. For example, if a new cutting plane 23', above cutting plane 23, is selected, a new fulcrum point O would be used (see FIG. 3B). The aiming motor 39 is controlled such that the head of x-ray is pointed at point O as it is moved from position A to position C as the tomo arm 20 is being moved about its predetermined path illustrated by line 43. At the same time the head 22 is moved along its predetermined path the cassette 46 is moved along its predetermined path represented by dash line 49 by cassette drive 54. The cassette drive may be of any conventional device as is commonly used in the art. However, an automatic filmer device as described in co-pending application filed simultaneously under Ser. No. 07/045,877, may be used and is hereby incorporated by reference herein. The path which cassette 46 takes is generally parallel to the top of the patient support. The movement and rate of speed of the cassette 46 is adjusted so that point O will remain in sychronism with the position of head 22 as it moves along its predetermined path. Accordingly, as the head moves along its predetermined path the film cassette 46 moves along its corresponding path 49 at the appropriate rate.

The speed and positioning of the film cassette is a matter of ordinary mathematics which one of ordinary skill in the art can determine. The particular rate and movement of head 22, tomo arm 20 and cassette 46 is controlled by control unit 77. Programming and selection of the apparatus is accomplished through the use of hand control 50 or foot control 51 which sends the appropriate signal to a microprocessor in the control unit 47. Applicant has found that in order to avoid computing the appropriate rate of movement of the tomo arm 20, aiming motor 39 and cassette drive 54, a precalculated set of values is determined for each of various cutting planes. Therefore, once a cutting plane is selected by the operator the motion and rate of speed to be taken by these parts will be preprogramed. This avoids mathematical computation by a microprocessor in control unit 47 during actual movement of the apparatus.

An important aspect of the present invention is that the film cassette 46 is not mechanically linked to either the motion of the tomo arm 20 or movement of the aiming motor 39. This avoids the unnecessary need of providing linkages, springs, counterweights and other equivalent mechanism required for matching the motion of these separate items. This, of course, reduces the complexity of the device required for proper synchronism of the parts, minimizes cost and improves reliability.

Various modifications to the present invention can be made without departing from the scope therein. For example, the path of the source of x-ray may be parallel as opposed to arcuate as illustrated. In such case the movement of the aiming motor would be controlled according to a different mathematical relation as the x-ray head moves along its path.

What is claimed is:

1. An apparatus for the taking of tomographic x-rays comprising:
    a frame;
    a generally planar patient support mounted to said frame;
    a tomo arm coupled to said frame for rotational movement about a fixed mechanical pivot point, said tomo arm extending generally transverse said patient support and having a distal end maintained a predetermined distance from said mechanical pivot point such that as said tomo arm pivots, said distal end moves in an arcuate path relative said patient support;

an x-ray source coupled to said tomo arm distal end and having means for rotational movement relative said distal end;

means for rotatably moving said x-ray source relative said tomo arm distal end such that x-rays emitted from said x-ray source will intersect a desired fulcrum point relative said patient support as said tomo arm rotates;

filmer means supporting an x-ray detector plate for movement in a plane generally parallel said patient support such that the x-rays emitted from said x-ray source will also intersect a desired exposure point on the x-ray detector plate as said tomo arm rotates; and means for correlating and controlling the rate and amount of movement of said tomo arm, x-ray source and filmer means independently of each other so as to provide a tomographic x-ray image along a preselected cutting plane in a patient placed on said patient support.

2. The apparatus of claim 1 further comprising:

an axle extending from said frame and defining said mechanical pivot point, said tomo arm being mounted to said axle, said tomo arm including a second distal end;

an arcuate member coupled to said tomo arm second distal end;

a motor suspended from said axle; and gear means coupling said motor to said arcuate member whereby to rotatably move said tomo arm about said mechanical pivot point in response to activation of said motor.

3. The apparatus of claim 1 further comprising:

means for pivotably mounting said patient support to said frame.

4. An apparatus for the taking of tomographic x-rays comprising:

a frame;

a generally planar patient support mounted to said frame;

an axle extending from said frame to define a mechanical pivot point;

a tomo arm mounted to said axle for rotational movement about said mechanical pivot point, said tomo arm extending generally transverse said patient support and having first and second distal ends, said first distal end being maintained a predetermined distance from said mechanical pivot point such that as said tomo arm pivots, said first distal end moves in an arcuate path relative said patient support;

an x-ray source coupled to said tomo arm first distal end and having means for rotational movement relative said first distal end;

means for rotatably moving said x-ray source relative said tomo arm first distal end such that x-rays emitted from said x-ray source will intersect a desired fulcrum point relative said patient support as said tomo arm rotates;

filmer means supporting an x-ray detector plate for movement in a plane generally parallel said patient support such that the x-rays emitted from said x-ray will also intersect a desired exposure point on the x-ray detector plate as said tomo arm rotates;

an arcuate member coupled to said tomo arm second distal end;

a motor suspended from said axle; and gear means coupling said motor to said arcuate member so as to rotatably move said tomo arm about said mechanical pivot point in response to activation of said motor.

5. The apparatus of claim 4 further comprising:

means for pivotably mounting said patient support to said frame.

* * * * *

UNITED STATES PATENT AND TRADEMARK OFFICE
CERTIFICATE OF CORRECTION

PATENT NO: 4,829,547

DATED : May 9, 1989

INVENTOR(S) : Lewis B. Mustain

It is certified that error appears in the above-identified patent and that said Letters Patent is hereby corrected as shown below:

Col. 4, line 25, "77" should be -- 47 --.

Signed and Sealed this

Twenty-seventh Day of February, 1990

Attest:

JEFFREY M. SAMUELS

Attesting Officer    Acting Commissioner of Patents and Trademarks